United States Patent [19]

Perelli

[11] Patent Number: 4,464,121
[45] Date of Patent: Aug. 7, 1984

[54] DEVICE FOR MEASURING FATIGUE EFFECTS

[76] Inventor: Layne P. Perelli, 19914 Encino Ridge, San Antonio, Tex. 78259

[21] Appl. No.: 372,771

[22] Filed: Apr. 28, 1982

[51] Int. Cl.³ .............................................. G09B 7/04
[52] U.S. Cl. .................................. 434/236; 273/1 E; 340/365 R; 434/258
[58] Field of Search .......... 272/129, DIG. 5, DIG. 6, 272/DIG. 7; 73/379; 273/1 G, 1 GC, 1 GE, 1 GH, 1 GI, 85 G, 237; 248/367; 434/236-238, 258; 340/365 VL, 365 R; 364/410, 706, 708

[56] References Cited

U.S. PATENT DOCUMENTS

| | | | |
|---|---|---|---|
| 2,947,092 | 8/1960 | Arnold et al. | 35/48 |
| 3,390,397 | 6/1968 | Friedlander | 346/33 |
| 3,473,239 | 10/1969 | Noseworthy | 35/21 |
| 3,526,971 | 9/1970 | Shipley | 35/9 |
| 3,685,169 | 8/1972 | Blau et al. | 35/8 R |
| 3,953,929 | 5/1976 | Hansel | 35/48 R |
| 3,971,142 | 7/1976 | Hollander | 35/22 R |
| 3,989,242 | 11/1976 | Shankel et al. | 434/258 |
| 4,010,556 | 3/1977 | Ellsworth et al. | 35/30 |
| 4,051,605 | 10/1977 | Toal et al. | 434/201 |
| 4,059,272 | 11/1977 | Pullman | 273/237 |
| 4,086,710 | 3/1978 | Craine | 35/22 R |
| 4,095,785 | 6/1978 | Conner | 273/1 GC |
| 4,149,257 | 4/1979 | Nakagiri et al. | 364/708 |
| 4,164,078 | 8/1979 | Goldman | 35/9 B |
| 4,189,912 | 2/1980 | Washizuka et al. | 364/708 |
| 4,209,735 | 6/1980 | Yoshida | 364/708 |
| 4,323,979 | 4/1982 | Johnston | 364/708 |
| 4,348,744 | 4/1981 | White | 434/237 |
| 4,372,557 | 2/1983 | Del Principe et al. | 273/85 G |

OTHER PUBLICATIONS

Perelli, "Effects of Fatigue Stressors on Flying Performance, Information Processing, Subjective Fatigue and Physical Cost Indicies During Simulated, Long-Duration Flight's Dissertion," 1980, pp. 83-123.

Primary Examiner—Richard C. Pinkham
Assistant Examiner—MaryAnn Stoll
Attorney, Agent, or Firm—Donald J. Singer; Stanton E. Collier

[57] ABSTRACT

A field portable performance assessment device having an adaptive information processing test programmed therein. The device is used to measure psychological data of personnel working in a real-world environment such as in an aircraft. A microcomputer drives a unique numeric-symbolic display that the test subject must respond to by activating a particular switch. The device is about the size of a hand-held calculator and operates on internal power for extended periods.

2 Claims, 5 Drawing Figures

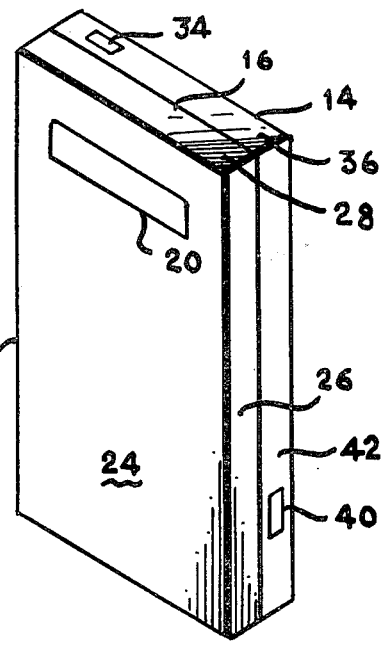
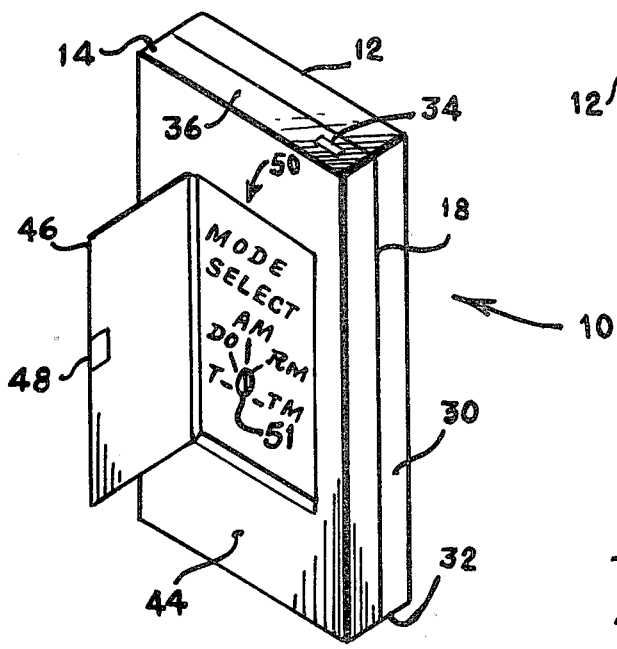
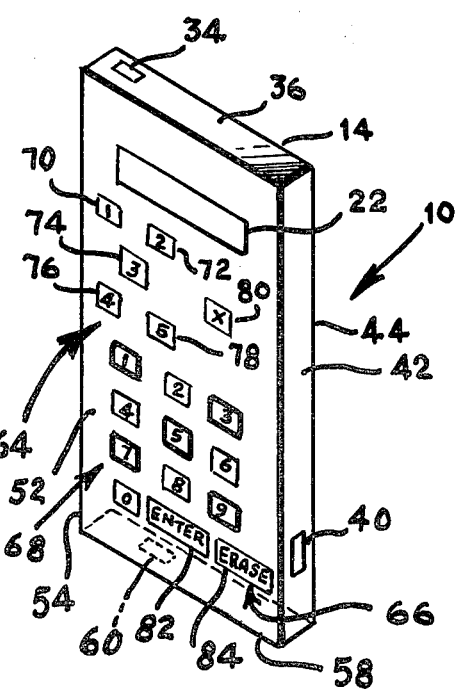

DEVICE FOR MEASURING FATIGUE EFFECTS

STATEMENT OF GOVERNMENT INTEREST

The invention described herein may be manufactured and used by or for the Government for governmental purposes without the payment of any royalty thereon.

BACKGROUND OF THE INVENTION

This invention relates to the field of psychological data collection, and more particularly, to a psychological testing device having an adaptive information processing test program therein.

Many of the past psychological testing devices have been so cumbersome that their use was confined to the laboratory. Although this may not be considered a problem in some circumstances, the artificial environment would defeat truly reliable performance assessment where the real-world environment cannot be factually replicated in the laboratory. These major obstacles make virtually impossible performance data collection because personnel were not actually engaged in their real-world tasks. This is especially so if personnel performance occurred in aircraft such as fighters where space is clearly at a premium, and the working environment is a substantial factor.

SUMMARY OF THE INVENTION

There currently exists, therefore, a need for a field portable performance assessment device that is about the size of a hand-held calculator and that can be programmed with a psychological test. The present invention overcomes the problems encountered in the past and described hereinabove.

The invention is a small, battery powered device about the size of a hand-held calculator. The device has a box-like case with a cover. The cover has a window therein to view the operating condition of the device. The case has an input/output terminal port, a power terminal port, an audible alarm port, a first multi-position display, a second display, a plurality of input switches, a plurality of mode selection switches, a plurality of control switches, and a microprocessor programmed to control the information presented in the displays. Responses via the input switches are stored in a data memory which is dumped to a processing computer after testing. The device has an internal power source and can operate for extended periods such as two weeks.

One object of the invention is to provide a field portable performance assessment device having programmed therein an adaptive information processing test for measuring psychological data in a real-world environment.

Another object of this invention is to provide a programmable self-contained device capable of storing data for an extended period of time such as two weeks.

Another object of this invention is to provide capability to capture and store a subject's report of feelings of fatique and workload.

Another object of this invention is to provide a field portable performance assessment device that interfaces with a general purpose computer for data processing.

Another object of this invention is to provide a field portable performance assessment device that facilitates ease of operation and acceptance by the subjects under study.

Another object of this invention is to provide a field portable performance assessment device that insures data integrity.

These and many other objects and advantages of the present invention will be readily apparent to one skilled in the art of psychological testing from a perusal of the claims and of the following detailed description of a preferred embodiment of the invention when considered in conjunction with the drawings.

BRIEF DECRIPTION OF THE DRAWINGS

FIG. 1 is a front pictorial view of the performance assessment device of this invention;

FIG. 2 is a back pictorial view of the performance assessment device of this invention;

FIG. 3 is a front pictorial view of the case of the performance assessment device of this invention;

FIG. 4 is an electronic functional block flow diagram of the field portable performance assessment device of this invention.

DETAILED DESCRIPTION OF THE INVENTION

Figure 5:
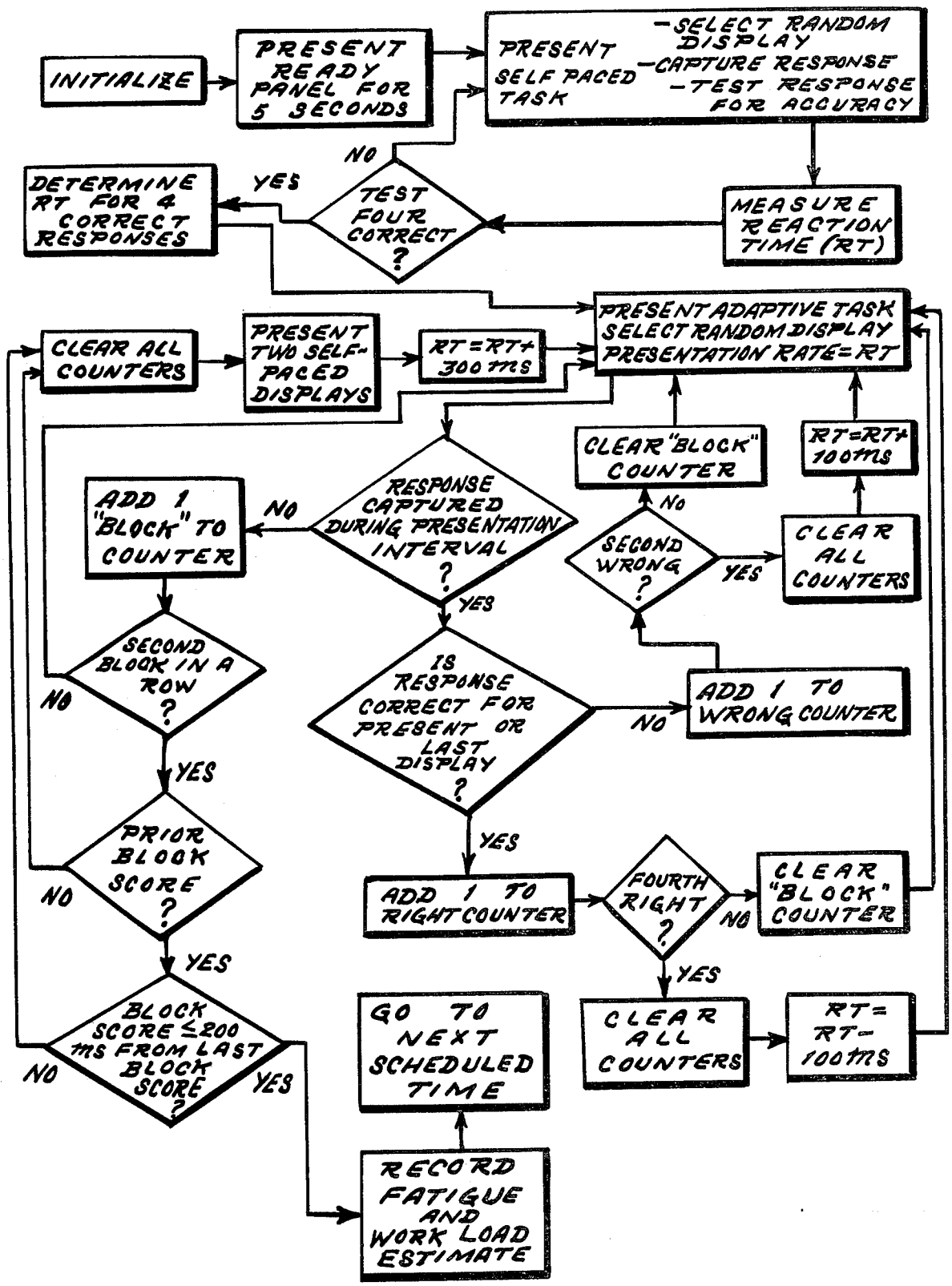
FIG. 5 is logic flow diagram of a preferred test stored within the performance assessment device of this invention.

Reference is made to FIGS. 1, 2 and 3 of the drawing which disclose in pictorial fashion a field portable performance assessment device 10 of this invention.

FIG. 1 illustrates field portable performance assessment device 10 having a cover 12 and a case 14. Both cover 12 and case 14 are constructed of durable, stiff plastic material. Cover 12 may be hinged to case 14 along a top joint 16, or a left side joint 18 (FIG. 2), or may be completely removable. Hinging is preferred since cover 12 may become misplaced and/or interfere with the operation of an aircraft. The method of hinging is conventional. Cover 12 has a window 20 therein so that the test subject can observe a date/time shown in a first display 22, shown in FIG. 3, to confirm the functioning of device 10 without opening cover 12. Instructions and subjective report scales may be mounted on cover 12. Cover 12 is useful also if there is an interlock between cover 12 and case 14 to prevent entry of data until required wherein opening of cover 12 would deactivate device 10. Cover 12 is constructed of a front panel 24, shaped essentially as a rectangle and four sides 26, 28, 30 (shown in FIG. 2), and 32 (not shown), shaped essentially as rectangles. Cover 12 and case 14 in the closed state waterproof the interior of device 10. The overall dimensions of device 10 are approximately four inches by seven inches by one and one half inches. Further, any ports in device 10 should be waterproofed to prevent water or moisture from invading the interior also. An input/output terminal port 34 is located on a top side 36 of case 14. The terminal located therein, not shown, can be connected to a general purpose computer 38, shown in FIG. 4. A conventional multi-pin male plug with cord attached can be inserted into port 34 for transferring information between device 10 and computer 38. In addition, an audible alarm port 40 is located on a right side 42 of case 14. An alarm therein sounds when the test subject is required to respond to the test programmed therein.

Referring to FIG. 2, the back of device 10 is illustrated. On a back side 44, a lockable lid 46, with a locking device 48, covers a mode select section 50. Operation of mode select section 50 is discussed at a later point hereinafter.

Referring to FIG. 3, case 14 is shown separated from cover 12. Case 14 has six rectangular sides, a front side 52, back side 44, top side 36, a left side 54, right side 42, and a bottom side 58 (not shown). A battery power terminal port 60 is included on bottom side 58, shown in ghost outline. A conventional battery charger, not shown, is connected into the battery power terminal to recharge batteries 62 in FIG. 4. Placement of battery power terminal port 60 on bottom side 58 is preferred since a battery charging receptacle, not shown, but conventional, could hold device 10 so that a trickle charger charges batteries 62; thus device 10 could be immediately used without waiting. Batteries 62 are of sufficient capacity to operate device 10 for a period of about two weeks. An indication of low battery power could be repeated audible alarms.

The other components forming part of case 14 and including various retainer brackets and the like included therein in order to hold the various components, as for example, batteries 62, could all be formed of a suitable plastic material, as for example polyethylene, polystyrene, polybutadiene or the like. Again, these various plastics which form cover 12 and case 14 and some of the components could all be formed in conventional plastic molding operations, as for example, thermoforming, injection molding, or the like. Again, other material as for example, metals, including aluminum or steel may also be employed for this purpose.

Front side 52 of case 14 has mounted therein first display 22, a second display 64, a plurality of input switches 68, and a plurality of control switches 66. First display 22 is a conventional multi-position display, preferably a liquid crystal display (LCD) to reduce power drain, having sufficient positions to display the date and time. Display 22 is viewed through window 20 of cover 12.

Second display 64 has a plurality of display positions, preferably LCD to reduce power drain, such as displays 70, 72, 74, 76, and 78 forming an "X". Display 74 is located at the center of the "X" and the other displays 70, 72, 76 and 78 are located on the arms of the "X". A display 80 is located to the right side of the "X". Displays 70, 72, 74, 76 and 78 have only one position for display of a symbol ranging from one to five. Display 80 also has only one position for display but a variety of symbols such as an "~", "#", "*", ">", or "[" can be displayed. Each symbol is assigned a particular number according to the adaptive information processing test such as 1≡#, 2≡*, 3≡>, 4≡~, and 5≡[. The numbers one to five can appear in any display 70, 72, 74, 76 and 78, no number being repeated. A symbol as noted above is displayed in display 80. The test subject prior to the test learns the relations between the symbols and the numbers. The test subject responds by pressing a particular push-button input switch 68 as noted below.

Input switches 68 are conventional, except that the 1, 3, 5, 7 and 9 positions are highlighted to form a similar "X" as noted in second display 64. Depending on the symbol displayed in display 80 and its corresponding numeric reference, the test subject would press the position in switches 68 that correspond with the position of the numeric reference of the symbol shown in second display 64. Input switches 68 can be used to enter other information such as date, time, subjective fatigue and workload response, etc.

Control switches 66 are press-button activated switches such as an ENTER 82 and an ERASE 84. Other control keys can be provided as needed.

Referring to FIG. 2, mode select section 50 has a mode switch 51 for selecting various modes of operation of device 10. T position is the training mode in which device 10 cycles continuously through a data collection period; DO is the data output mode used to transfer the data memory directly to computer 38; AM is the alarm mode normally used to select the desired data collection period schedule and to set the correct date and time; RM is the research mode used to collect data in the field; and TM is the test mode used as an internal self-check to assure proper functioning.

Referring to FIG. 4, the electronic functional block diagram of an electronic processing means 91 of device 10 is illustrated. Microcomputer 86 is powered by internal battery power 62 and communicates through input-/output device 90 including first display 22, second display 64, input switches 68, control switches 66, alarm 40, mode select section 50, and input/output terminal port 34. Memory retention by data storage memory and program memory is required when device 10 is powered down. General purpose computer 38 is connected to input/out terminal port 34 so that data stored may be dumped into computer 38 for data processing. Further computer 38 can reprogram device 10 so that a variety of testing programs may be used. A preferred program for device 10 is the adaptive information processing test having the logic flow diagram of FIG. 5 to be discussed hereinafter.

The means of connecting input/out device 90, computer 38, microcomputer 86 and power 62 is conventional and is therefore not described in any further detail herein. The devices making up field-portable performance assessment device 10 are conventional such as microcomputer 86 which can be composed of several integrated circuit chips. The switches of device 10 are conventional and provide only one input signal upon each actuation and must be released and pressed again before the switches can provide another input signal. The displays are conventional in form and can be light-emitting diodes, liquid crystal displays, etc. with the LCD preferred because of lower power consumption.

To develop a task sensitive to fatigue stressors, the following factors have been taken into account in developing the adaptive information processing test used in device 10:

(1) Monotonous tasks and those with high complexity or difficulty but relatively low interest are highly sensitive to sleep loss;

(2) Self-paced tasks show little loss in accuracy but total response time increases with sleep loss;

(3) As the time available for making a response increases, the task becomes less sensitive;

(4) The longer a task lasts, the more sensitive it is to sleep loss;

(5) Tasks measuring blocking or gaps tend to be most sensitive to sleep loss;

(6) Tasks requiring continuous performance, not providing breaks or rest pauses, are more sensitive to sleep loss;

(7) Tasks requiring minimal physical activity are more sensitive to sleep loss;

(8) Sleep loss tends to increase reaction time (RT), but not consistently;

(9) Knowledge of results (KR) increases resistance to sleep loss;

(10) Newly acquired skills or tasks that have not been well practiced or have not reached a plateau in learning are suceptible to sleep loss.

Tasks making severe short-term memory demands are also susceptible to sleep loss, but this factor is not to be incorporated into the test.

In order to develop a task which is useable in field operations, the following further practical requirements have been considered in developing the adaptive information processing test of device 10:

(1) The test should be easily and quickly learned to a stable baseline level;
(2) The duration of the test should be as short as possible so as not to induce any significant, additional workload or fatigue on the operator and to keep interference with ongoing operations to a minimum;
(3) The test should be easy to administer;
(4) The test should be resistant to spoofing or guessing;
(5) The test should be as resistant to changes in motivation as possible;
(6) The test should be nonauditory in nature because of varying noise levels in operational settings and varying degrees of hearing loss found in operators;
(7) The test apparatus should be capable of being made highly portable with its own independent power supply;
(8) The measurement technique must be generally acceptable to the population under investigation.

In order to satisfy the operational requirements as well as possible with a test that would be sensitive to sleep deprivation, the inventor developed a complex, five-choice visual RT task and incorporated it into a computer-based adaptive logic presentation system. It has been termed the Adaptive Information Processing Test.

The distinctive feature of an adaptive logic system is that the subject's response is fed back to modify the difficulty level of the next stimulus presentation, based on how well the subject is performing. One of the earliest uses of this concept was the development of programmed instruction techniques in which the training material was presented in an order according to a predetermined criterion of student progress.

In an adaptive tracking task, during the course of a continuous tracking period, the subject's integrated error score is used to adjust the difficulty level of the task to maintain the error score at a preset criterion. It has been found that this technique requires less time to train the subject to a baseline criterion than fixed tracking. There are several reasons for this. First, training time is more productive because little time is wasted giving the subject practice at a difficult level which is either already mastered or entirely above his present capability. Secondly, and just as important, the subjects maintain high motivational levels on this type of task. They are given an optimum challenge no matter how hard they try. They cannot succeed; yet they never experience severe failure. The adaptive tracking task has been extended to jet flight stimulator training. The turbulence input to a fixed-base Universal Digital Operational Flight Trainer Tool was modified continually as a function of how well the students were able to hold the simulated aircraft within a given criterion of reference altitude. It was found that when compared to a group of students conventionally trained, they improved more rapidly and made fewer errors. There was also some indication that, rather than having developed problems in controlling a secondary variable, such as airspeed, they had developed a control strategy which reduced other errors as well.

A variation of adaptive technology has been applied to the secondary task approach to assess reserve capacity. In this case the difficulty of the secondary task is adjusted on the basis of primary task performance in an attempt to quantify and control the operator effort expended in maintaining various levels of performance.

In the adaptive task developed, refer to FIG. 5, and used in field portable performance assessment device 10, the rate of stimulus presentation is a function of the latency of the prior response time and error rate. The computer increases the rate of presentation until the subject's information processing capacity is overloaded. This presentation rate is taken as the test subject's threshold of information processing capacity. There are two sources of overload in this task: first, the processing threshold at which the subject can no longer keep up with the presentation rate; and second, a block in which the subject cannot respond for a short period of time, regardless of the presentation rate. To the extent that the latter block is not indicative of the true information processing threshold, the subject is given a second chance to lower the threshold. But as the blocking becomes more frequent with fatigue, it will become the predominant source of overload.

The task consists of the following steps: The subject must first learn an association between five symbols and a corresponding numeral from 1 to 5. Each trial consists of a display of one of the symbols and all give numbers in random pattern. The test subject must press a button corresponding to the location of the number which has been associated with the displayed symbol. This information processing task requires four subtasks: (a) recognition of the symbol; (b) recall of the number-symbol association from long-term memory; (c) search for the location of the correct number; and (d) the motor response to push the location of the correct button. It is felt that this task provided the required complexity level yet would not require a lengthy training period. Guessing is easily detected since the probability of responding correctly by guessing is only 0.2.

The adaptive logic of the task is as follows, referring to FIG. 5: the subject is initially presented displays in a self-paced mode to which he responds as fast as he can; the computer averages the reaction time (RT) for the first four correct responses and from this point on the rate of presentation of the panels is computer-paced; the computer presents each panel initially for the duration of the self-paced RT score; and the determination of the subject's initial response capability saves task presentation time since if the task was started at a fixed presentation interval, it would have to be slow enough to encompass the slowest initial response time expected from any subject at any level of fatigue.

The task is designed to be simple enough that the subject will almost always respond correctly. Wrong answers are scored primarily to protect against those who might try to guess. If he makes two errors before he gets four correct, the presentation rate is reduced by 100 ms. If he gets four right before he gets two wrong, the presentation rate is increased by 100 ms, up to the rate where he blocks. A block is defined as the presentation of two panels in a row to which the subject does not respond. The presentation rate at which this occurs is recorded. When a block is detected, two self-paced presentations are made to allow the subject to recover his concentration. However, there is no rest pause provided during this period. The speed of presentation is then reduced by 300 ms and the adaptive presentation logic is continued. The duration of the task is variable; it lasts only as long as it take for the subject to make two successive blocks within 200 ms of each other.

Thus the task contains both paced and unpaced components. It is primarily computer-paced but it responds to the overload condition by slowing the presentation rate just as the subject would if he were in control.

The average response time when blocking occurs has been found to be about 600 ms. From pilot studies it has been found that the total task time required for a subject to block within the prescribed limits is normally about 60 seconds and the subject will normally produce from two to four blocks to reach criterion. Note that the definition of a block is relative in that it is based on the ongoing presentation rate.

The use of a high-speed computer is critical to this type of adaptive technology since it permits a continuous task to be presented to the subject, scored, and modified, with delays which are imperceptible to the subject. The computer utilizes overload information to adapt the speed of presentation to the information processing capability of the subject. But the computer is capable of presenting and scoring the task faster than any subject can keep up with, and thus can always present the displays and score the responses at rates faster than the subject's processing threshold speed.

Numbers 1 to 5 appear randomly in display section 64 on the left side of display 64. One of the five symbols appears on the right of display 64: #, *, ~, >, or [. There are 120 possible number patterns that can be generated with 5 numerals. When paired with one of the five symbols, 600 unique stimulus patterns are created.

In an initial pilot study of this test, two sets of randomized displays containing subsets of four data files were constructed in the following manner: first, 300 of the unique displays were randomly assigned to the first set; the remainder were assigned to the second; next each group of 300 was randomly assigned to 1 of 4 subsets, 75 to each subset; then 10 from the total display set were randomly selected and assigned to each subset for a total of 85 displays per subset. The random selection process is arranged so that each symbol and each correct response location on the push-button panel occurred 17 times in each data file of 85 stimulus patterns. Additionally, the data file is inspected and when two identical symbols appeared in a row, the second is randomly assigned to a new location in the list. This is done in order to make it easier for a subject to recognize that a new trial is being presented. Both sets of files were stored in the computer.

The subjects were required to memorize the following number-symbol associations: 1≡#, 2≡*, 3≡>, 4≡~, and 5≡[. The subject's task was to press input switches 68 which corresponded to the position of the numeral associated with the symbol displayed in display 80. See FIG. 3. The subject was instructed to continue responding to the task, as rapidly as possible, as long as displays were presented.

In addition, the subjects were instructed to respond only when they knew the correct response. A subject learned that wrong answers slowed the presentation rate, and that the task would not end until he caused it to speed up to the point that he was unable to keep up with it when attempting to give correct answers.

Another feature of this device is that every time the Adaptive Information Processing Test is completed, the subject can enter his subjective feelings of fatigue by pressing one of the input switches 68. Refer to FIG. 5. Input switches 68 labeled one to seven correspond to seven levels of a fatigue checklist, printed on the inside of cover 12. The subject's response will be stored along with his corresponding information processing test score. He would then enter his subjective feeling of his current workload estimate, also from a scale of one to seven using a workload checklist printed on the inside of cover 12. The device has a programmable audio alarm in alarm port 40 to alert the subject to each data collection period. There is a capability for a maximum of 16 data collection periods per day for 14 days for a total of 224 data collection periods which will be stored in the device. Data to be stored each period consists of an adaptive information processing score, a subjective fatigue score, a subjective estimate of workload, and a code to identify the date and time of the data collection period.

Obviously, many modifications and variations of the present invention are possible in light of the above teachings and it is therefore understood that, within the scope of the disclosed inventive concept, the invention may be practiced otherwise than specifically described.

What is claimed is:

1. A device for measuring fatigue under varying workloads in a real world environment, said device having an adaptive information processing test programmed therein, said device comprising:

a case, said case having therein:

a first display, said first display providing date and time information during a testing period;

a second display, said second display consisting a symbol display and a numeric display, said symbol display presenting one of a plurality of symbols upon a computer command, said numeric display consisting of five digit displays arranged in an "X" pattern, one of said five digit displays being located on each arm of said "X" and one located at the center of said "X", each of said symbols corresponding to a number displayed in one of said digit displays as predetermined by said adaptive information processing test whereby a user of said device must know what number corresponds to each of said symbols;

a plurality of numeric input switches, said numeric input switches located on a front side of said case and positioned below said second display, said input switches having numerals printed thereon, one numeral per switch, said numerals ranging from zero to nine, numeric input switches one, two, three located in a first row, numeric input switches four, five, six located in a second row, numeric input switches seven, eight, nine located in a third row, and numeric input switch zero located in a fourth row, said first, third, fifth, seventh, and ninth numeric input switches highlighted from said other switches so as to form an "X" pattern similar to the "X" formed by said numeric display of said second display;

control switch means located on said front side of said case and positioned near the bottom of said numeric input switches, said control switch means being able to enter and erase data entered on said numeric input switches;

a mode select switch that controls the functioning of said device;

an input/output terminal for connecting electronically said device to a general purpose computer for the purpose of programming and data processing;

an audible alarm for warning said user upon the occurrence of predetermined conditions, a battery charging port for charging an internal battery; and a microcomputer, said microcomputer operably connected to said first display, said second display, said numeric input switches, said control switch means, said mode select switch, said input/output terminal, said audible alarm, and said internal battery, said microcomputer programmed with said adaptive information pocessing test, said microcomputer causing one of said symbols to appear in said symbol display of said second display and numbers to appear in said numeric digit display where one of said numbers corresponds to said symbol being displayed at that time, said user being required to remember the correspondence between said symbol and said number, said user noticing the position of said number in said "X" of said numeric digit display, and said user pushing a numeric input switch that corresponds with said portion of said number that corresponds with said symbol being displayed at that time, said user being required to repeatedly accomplish the above as programmed in said microcomputer, said microcomputer storing the results of each response for input to said general purpose computer; and a cover, said cover having a window therein to view said first display, said cover attached to said case.

2. A device for measuring fatigue as defined in claim 1 wherein said microcomputer further collects data relating to a subjective fatigue score and a subjective estimate of workload entered by said user.

* * * * *